(12) United States Patent
Servati et al.

(10) Patent No.: US 10,895,510 B2
(45) Date of Patent: Jan. 19, 2021

(54) CORE-SHELL NANOFIBER TEXTILES FOR STRAIN SENSING, AND METHODS OF THEIR MANUFACTURE

(71) Applicant: TEXAVIE TECHNOLOGIES INC., Vancouver (CA)

(72) Inventors: Peyman Servati, Vancouver (CA); Frank K. Ko, Vancouver (CA); Saeid Soltanian, North Vancouver (CA); Amir Servati, Coquitlam (CA)

(73) Assignee: TEXAVIE TECHNOLOGIES INC., Vancouver (CA)

( * ) Notice: Subject to any disclaimer, the term of this patent is extended or adjusted under 35 U.S.C. 154(b) by 0 days.

(21) Appl. No.: 16/658,423

(22) Filed: Oct. 21, 2019

(65) Prior Publication Data

US 2020/0225101 A1  Jul. 16, 2020

Related U.S. Application Data

(63) Continuation of application No. 15/350,922, filed on Nov. 14, 2016, now Pat. No. 10,481,022, which is a continuation of application No. 14/120,443, filed on Apr. 3, 2014, now Pat. No. 9,494,474.

(60) Provisional application No. 61/808,096, filed on Apr. 3, 2013.

(51) Int. Cl.
| | |
|---|---|
| *A61B 5/021* | (2006.01) |
| *A61B 5/08* | (2006.01) |
| *A61B 5/024* | (2006.01) |
| *B82Y 10/00* | (2011.01) |
| *G01L 1/20* | (2006.01) |
| *G01L 1/22* | (2006.01) |
| *A61B 5/11* | (2006.01) |
| *A61B 5/00* | (2006.01) |

(52) U.S. Cl.
CPC .............. *G01L 1/205* (2013.01); *A61B 5/021* (2013.01); *A61B 5/08* (2013.01); *A61B 5/11* (2013.01); *A61B 5/6804* (2013.01); *B82Y 10/00* (2013.01); *G01L 1/2287* (2013.01); *A61B 5/024* (2013.01)

(58) Field of Classification Search
None
See application file for complete search history.

(56) References Cited

U.S. PATENT DOCUMENTS

| | | | | |
|---|---|---|---|---|
| 9,259,175 | B2* | 2/2016 | Stafford | A61B 5/14503 |
| 9,322,121 | B2* | 4/2016 | Dunne | D05B 97/12 |
| 9,386,684 | B2* | 7/2016 | Sime | H05K 1/0373 |
| 9,816,799 | B2* | 11/2017 | Keller | G01L 1/225 |
| 10,251,266 | B2* | 4/2019 | Seo | B32B 5/06 |
| 10,470,674 | B2* | 11/2019 | Tanriover | G01S 5/18 |
| 10,481,021 | B2* | 11/2019 | Pan | A41D 25/00 |
| 10,602,965 | B2* | 3/2020 | Connor | G06F 3/014 |
| 10,653,190 | B2* | 5/2020 | Longinotti-Buitoni | A42B 1/046 |

(Continued)

*Primary Examiner* — Natalie Huls
*Assistant Examiner* — Jermaine L Jenkins

(57) ABSTRACT

This invention pertains to a low cost, low noise strain sensor based on a web of continuous core-shell nanofibers with conductive shell and mechanically robust core that can be attached or embedded on a variety objects for directional monitoring of static or dynamic changes in mechanical deformation and pressure. This is a low cost, highly sensitive strain sensor, with low noise and ease of integration for different applications from synthetic tactile skins, to vibrational and health monitoring.

21 Claims, 9 Drawing Sheets

(56) References Cited

U.S. PATENT DOCUMENTS

2017/0224280 A1\* 8/2017 Bozkurt ................. A61F 13/42
2018/0154140 A1\* 6/2018 Bouton ................ A61B 5/1127

\* cited by examiner

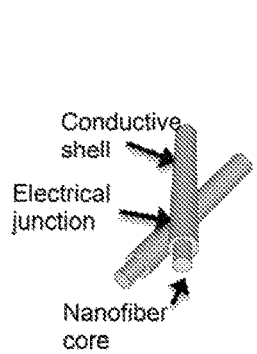
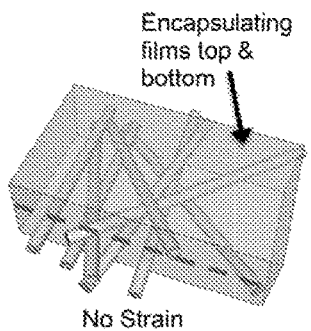
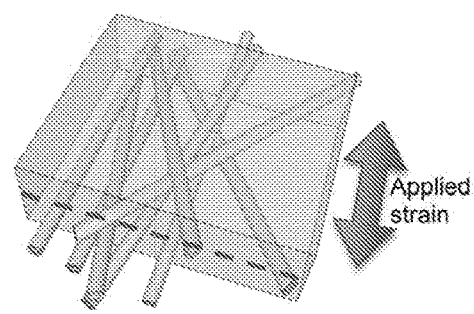
FIG. 1A    FIG. 1B    FIG. 1C
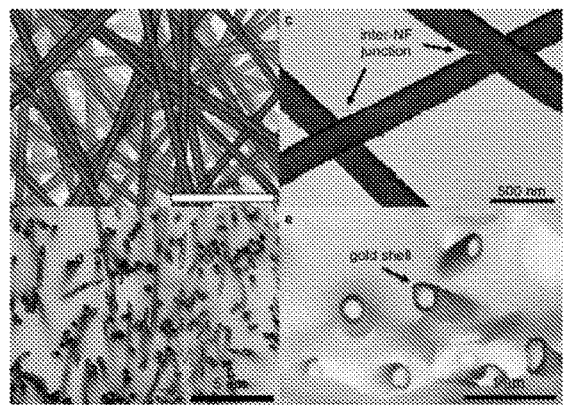
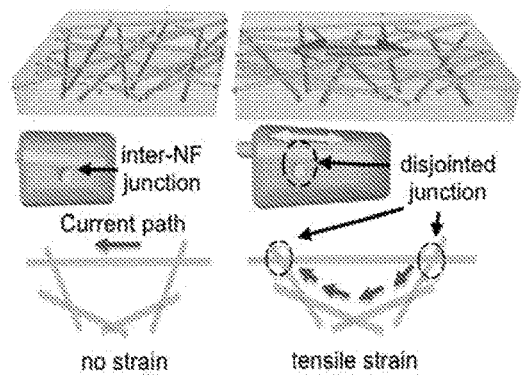
FIG. 1D    FIG. 1E
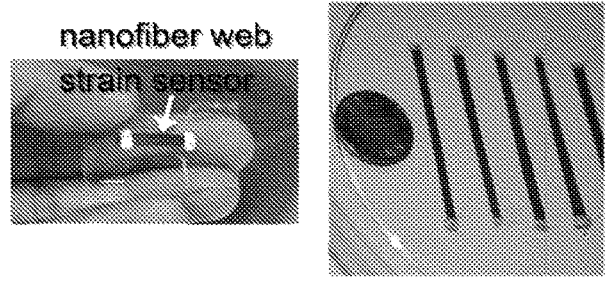
FIG. 2

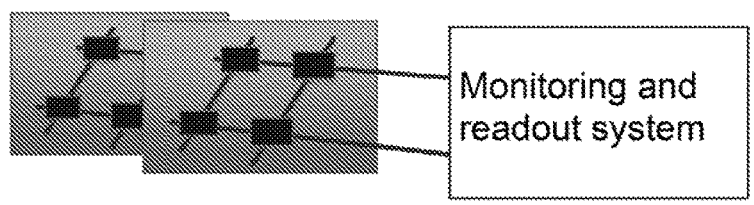
FIG. 7A
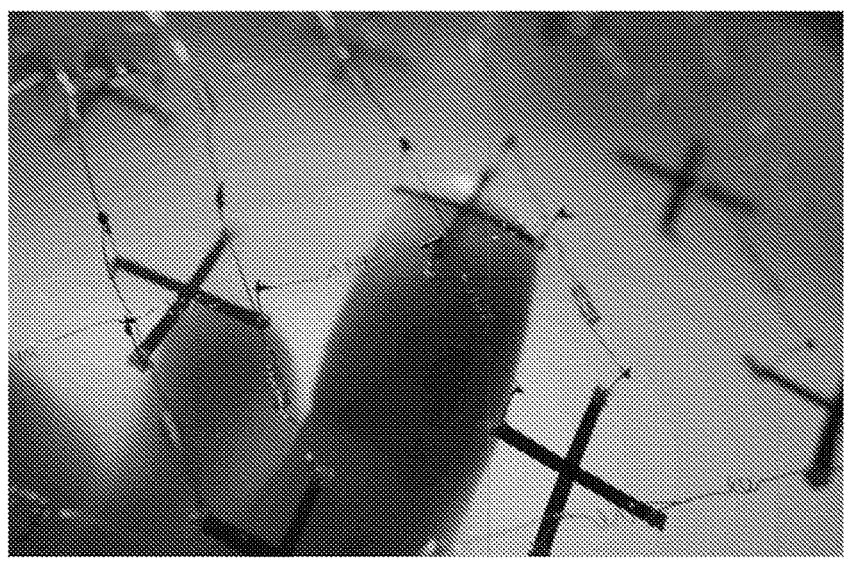
FIG. 7B
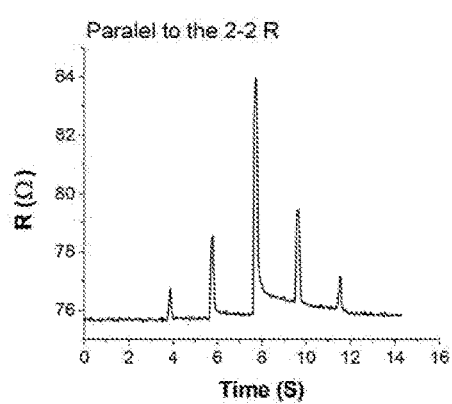
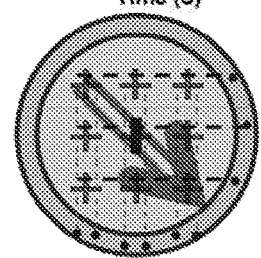
FIG. 7C
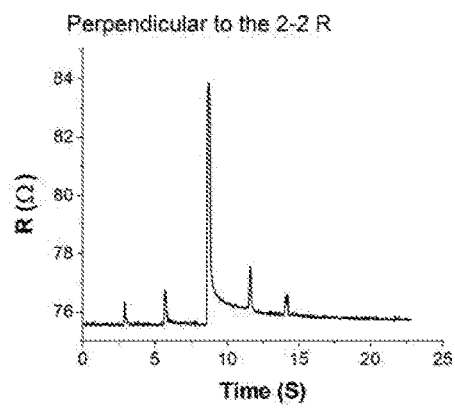
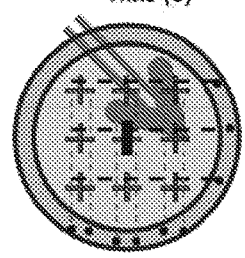
FIG. 7D

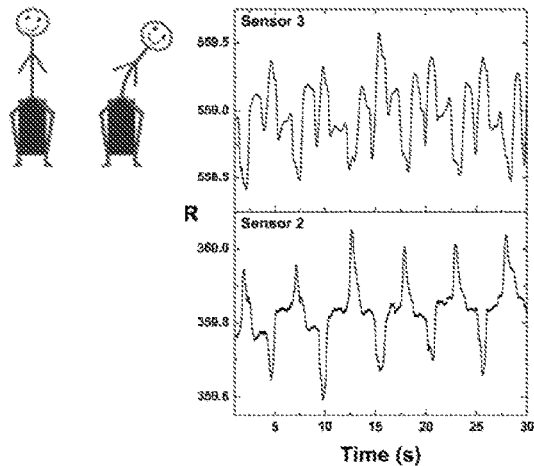
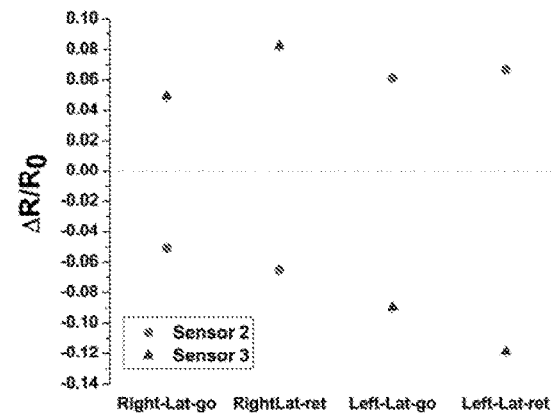
FIG. 10A  FIG. 10B
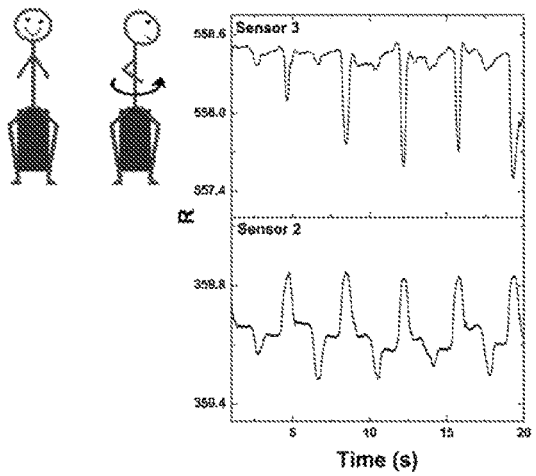
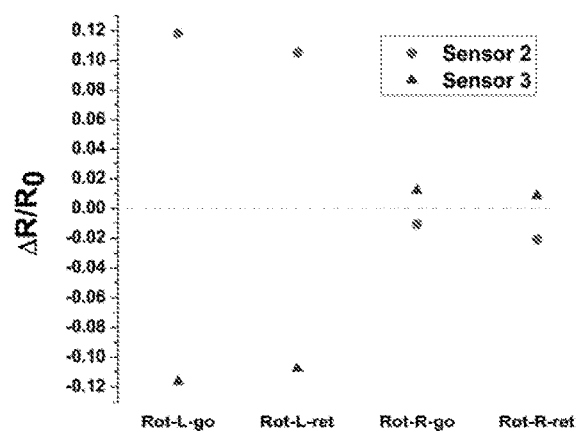
FIG. 11A  FIG. 11B

CORE-SHELL NANOFIBER TEXTILES FOR STRAIN SENSING, AND METHODS OF THEIR MANUFACTURE

BACKGROUND OF THE INVENTION

1. Field of Invention

This invention relates to highly sensitive strain sensor devices made from encapsulated core-shell nanofiber meshes. The sensor films can be adhered to or embedded in a variety of objects and textiles for monitoring of deformation, pressure and vibrations for tactile, structural health, living object health, and vital sign monitoring with accuracy, low cost and easy read out.

2. Description of Related Art

Natural systems, such as human skin, are covered with sensors of mechanical deformation or pressure to provide the "sense of touch". An electronic skin that can provide tactile sensing to synthetic products has a wide range of applications, including measurement of mechanical strain and cracks for monitoring of aging infrastructure (such as buildings, skyscrapers, bridges, dams, pipelines, turbine blades and drain system), sensing mechanical forces on composite body of aviation or other transportation vehicles for structural health monitoring and safety, vibrational sensors for monitoring operation of complex machinery, and touch sensors for human-media devices such as e-books and smart/mobile phones. In addition, by attaching such devices to human body or clothing in form of implantable or wearable electronics, vital health signs such as heartbeat, breathing, muscle movements and blood pressure can be monitored through smart wound coverings or smart fabric/clothing.

Conventional strain and pressure sensors use piezoelectric ceramics (e.g., lead zirconate titanate (PZT)), piezoelectric polymers (e.g., polyvinylidene fluoride (PVDF)), pyroelectric ceramics (e.g., barium titanate ($BaTiO_3$) and piezoresistive semisonductors (e.g., polysilicon). The sensors provide a gauge factor ranging from 0.0001 to 30. These materials are costly, bulky, can have toxic elements such as lead, and have complex deposition and post processing processes. Commercial PZT sensors are costly, rigid and brittle, toxic and environmental unfriendly, and are hard to manufacture over large area and at low cost. Metallic strain gauges and piezoresistive sensors have smaller gauge factors and small threshold for sensitivity. Strain sensors based on aligned and random meshes of nanowires (NWs), carbon nanotubes (CNTs) and CNT composites have been demonstrated but suffer from large area scalability, reproducibility of response and low gauge factors in the range of 0.0001-2.

Some patents that describe the current state of the art for systems for low cost strain sensors and sensors for electronic skin are as follows: U.S. Pat. No. 8,159,235 (Lynch et al., 2012) have shown electrical impedance tomography of nanoengineered thin films. U.S. Pat. No. 8,108,157 (Chase et al., 2012) have shown electrospun fibrous nanocomposites as permeable, flexible strain sensors. These sensors made of conductive fibres whose resistance change due to narrowing of the current path between two electrodes by stretching. The sensitivity, low resistance and repeatability of encapsulated nanofiber mesh presented in this invention is significantly higher that allows applications for wearable electronics and structural health monitoring not useful in the prior art. U.S. Pat. No. 7,921,727 (Rice, 2011) have shown sensing system for monitoring the structural health of composite structures.

SUMMARY OF THE INVENTION

The invention described here presents a strain sensor device based on encapsulated core-shell nanofiber mesh and the method of manufacture. The sensor device provides a high gauge factor (in excess of 60, expected from piezoelectric sensors), has a low cost and scalable manufacturing process, provides low noise measurable resistance suitable for low power applications and demonstrates repeatable fast response to transient changes in strain. The sensor device has a thin thickness (for instance can be as small as less than 0.3 mm) and can be adhered, laminated, attached or embedded on different objects or substrates so as to provide information on static and dynamic mechanical strain and stress that are present in an object under test. The sensitivity to strain arises by encapsulating the core-shell nanofiber mesh between to elastomer films that are cured together to form an encapsulated nanofiber mesh. The elastomer surrounding the nanofiber mesh responds to the external strain and connect or disconnect the plurality of junctions formed between the conductive shells of nanofibers.

An embodiment of this invention presents the use of the sensor device for dynamic vibrational monitoring in mechanical equipment and machinery. If attached or incorporated infrastructures, including but not limited to, building and bridges, the sensor device can be used to monitor loading and usage of structures, aging and formation of cracks for longevity and reliability of the infrastructures, as another embodiment of this invention. When this sensor is placed on a human or animal body part, as another embodiment of this invention in form of wearable electronics or electronic skin, it can provide information such as muscle movements, heartbeat, breathing, body movement, blood pressure, tissue contractions, tremors, including but not limited to Parkinson's tremors, seizures, by measuring the transients in mechanical deformations of the skin.

Various embodiments of the invention provide a strain sensor device comprising: a plurality of continuous nanofibers operable to conduct an electric current in a desired direction, wherein each nanofiber has a core-shell structure with a conductive shell having a plurality of electrical junctions with the conductive shell of an overlapping nanofiber, wherein the plurality of nanofibers are embedded at the interface of first and second encapsulating films that are adhered together, whereby a change in resistance that is encountered by the electric current provides an indication of tensile and compressive mechanical strains. At least two electrical contacts may be formed between the plurality of nanofibers and electrical wirings or an embedded electrode at an interface of the two encapsulating films, wherein the wires may be operable to apply and measure electrical voltage or current to evaluate changes in the resistance of the device to determining the strain in a desired direction. The location of the contacts may be used to determine the direction of the current flow in the nanofibers. The electrical contacts may be connected to external wiring for monitoring resistance. The nanofibers may be of different densities. The strain sensor device may further comprise a means for transmitting an output signal representing the change in resistance.

Various embodiments of the invention provide a plurality of strain sensor devices as described above, for attachment on a surface of a rigid, flexible or stretchable object for monitoring changes in mechanical strain and stress of the system. The plurality of strain sensor devices may be for monitoring one or more of strain, sound, ultrasound, impact, and tactile force. However, a person skilled in the art will understand that the changes in mechanical strain and stress of the system that can be measure with the strain sensor devices need not be limited to the above.

Various embodiments of the invention provide a system for monitoring changes in mechanical strain and stress, wherein the system comprises a plurality of strain sensor devices as described above that are attached on a surface of a rigid, flexible or stretchable object.

Various embodiments of the invention provide a method of fabricating a strain sensor device. The method comprises: depositing on a first encapsulating film a nanofiber core by continuous fiber deposition from a polymer solution or a composite solution to form a continuous core of nanofibers; depositing a conductive shell on the continuous core to form core-shell nanofibers; cutting the core-shell nanofibers to a required size and dimension; establishing electrical contacts with the core-shell nanofibers; and depositing a second encapsulating film on the core-shell nanofibers. The continuous fiber deposition may include, but is not limited to, electrospinning. The conductive film may be deposited using sputtering or electrodeposition, or any other suitable method. The method may further comprise connecting the electrical contacts to external wiring to monitor resistance. The conductive shell may be deposited on selected areas of the continuous core to form core-shell nanofibers with patterned sensitive areas.

Various embodiments of the invention provide a method of fabricating a core-shell structure of continuous nanofibers for a strain sensor device. The method comprises: electrospinning a plurality coaxial core-shell nanofibers from a polymer solution for the core, and a conductive solution for the shell, cutting the core-shell nanofibers to a desired size and dimension; and making electrical contacts to the plurality of nanofibers.

Various embodiments of the invention provide a method of fabricating a strain sensor device. The method comprises fabricating a core-shell structure of continuous nanofibers according a method as described above, and depositing and curing encapsulating films on the core-shell structure of continuous nanofibers.

Various embodiments of the invention provide a rigid, flexible or stretchable object comprising one or more strain sensor devices as described above, wherein the strain sensor devices are for monitoring of strain, sound, ultrasound, impact, tactile and other changes in mechanical strain and stress on the object.

Various embodiments of the invention provide a biaxial strain sensor device. The device comprises a first and a second plurality of continuous nanofibers, wherein each nanofiber has a core-shell structure with a conductive shell and a mechanically robust core. The conductive shell of each nanofiber has a plurality of electrical junctions with the conductive shell of other overlapping nanofibers in the same plurality of nanofibers. The first plurality of nanofibers is operable to conduct a first electric current flowing in a first direction and the second plurality of nanofibers is operable to conduct a second electric current in a second direction generally perpendicular to or angled to the first direction. The first plurality of continuous nanofibers is placed at the interface of a first and a second encapsulating films that are attached together, wherein the second plurality of nanofibers are placed at the interface of the second and a third encapsulating films that are adhered together. The electrical resistance encountered by the first electric current provides information for the mechanical strain in the first direction and electrical resistance encountered by the second electric current provides information on the mechanical strain in the second direction.

Various embodiments of the invention provide a biaxial strain sensor device. The device comprises a first and a second plurality of continuous nanofibers. The first plurality of nanofibers is operable to conduct a first electric current in a first direction. The second plurality of nanofibers is operable to conduct a second electric current in a second direction generally perpendicular or angled to the first direction. Each nanofiber has a core-shell structure with a conductive shell and a core, wherein the conductive shell of each nanofiber has a plurality of electrical junctions with the conductive shell of overlapping nanofibers in the same plurality of nanofibers. The first plurality of continuous nanofibers is placed at the interface of first and second encapsulating films that are attached together. The second plurality of nanofibers is placed at the interface of the second and a third encapsulating films that are adhered together. Electrical resistance encountered by the first electric current provides information for the mechanical strain in the first direction, and electrical resistance encountered by the second electric current provides information on the mechanical strain in the second direction.

Various embodiments of the invention provide a sensor device as described above, wherein two electrical contacts are made to the first plurality of nanofibers to connect the first plurality to two external wires at the interface of the first and second encapsulating films, and two electrical contacts are formed to the second plurality of nanofibers to connect the second plurality to two external wires at the interface of the second and third encapsulating films. The wires are operable to apply and measure electrical voltage and current to evaluate changes in the resistance of the device for determining the strain in the first direction.

Various embodiments of the invention provide a plurality of strain sensor devices as described above, wherein the strain sensor devices are positioned in crosses for monitoring location dependent strain in two directions on the surface of a rigid, flexible or stretchable object to monitor strain, sound, ultrasound, impact and other changes in mechanical strain and stress of the system.

Various embodiments of the invention provide a rigid flexible or stretchable object comprising a plurality of strain sensor devices as described above.

Various embodiments of the invention provide a use of a strain sensor device or a plurality of strain sensor devices as described above for monitoring of a voltage or current while applying a current or voltage, respectively, in a limb for looking at movements and contractions of limbs and muscles for health monitoring applications.

Various embodiments of the invention provide a use of a strain sensor device, or a plurality of strain sensor devices as described above for monitoring of pulse rate and pulse waveform.

Various embodiments of the invention provide a use of a strain sensor device, or a plurality of strain sensor devices as described above for monitoring spine and back movements and muscle contraction.

Various embodiments of the invention provide a use of a strain sensor device, or a plurality of strain sensor devices as described above for monitoring Parkinson's tremors.

Various embodiments of the invention provide a use of a strain sensor device, or a plurality of strain sensor devices as described above for monitoring seizures.

Various embodiments of the invention provide a use of a strain sensor device, or a plurality of strain sensor devices as described above for monitoring seizures.

Various embodiments of the invention provide a plurality of compliant strain sensors attached to the lower and upper back, for monitoring of spine and back movements and muscle contraction for temporal posture monitoring.

Various embodiments of the invention provide a plurality of compliant strain sensors attached to a limb or worn in form of clothing or a cuff on a limb for monitoring of Parkinson's tremors of the limb over time.

Various embodiments of the invention provide a plurality of compliant strain sensors attached to patient's body or clothing for monitoring of seizure's attack over time.

Various embodiments of the invention provide a plurality of strain sensors that are placed on a single compliant film or fabric for monitoring of multiple health signals such as pulse rate and waveform, body temperature, muscle movements, and chemicals released from body over time. The monitored signals can be used at one place for diagnosis and treatment.

Various embodiments of the invention provide a plurality of compliant strain sensors attached on epidermis on top of a pulsing vein, a wrist artery, a radial artery, dorsal pedis artery, brachial artery, carotid artery, temporal artery, femoral artery, for monitoring of pulse rate and pulse waveform over time for health monitoring applications. Alternatively, local pressure may be applied to create a pulse in other arteries including but not limited to digital arteries.

Various embodiments of the invention provide a plurality of compliant strain sensors attached to the lower and upper back, for monitoring of spine and back movements and muscle contraction for temporal posture monitoring.

Various embodiments of the invention provide a plurality of compliant strain sensors attached to a limb or worn in form of clothing or a cuff on a limb for monitoring of Parkinson's tremors of the limb over time.

Various embodiments of the invention provide a plurality of compliant strain sensors attached to patient's body or clothing for monitoring of seizure's attack over time.

Various embodiments of the invention provide a plurality of strain sensors that are placed on a single compliant film or fabric for monitoring of multiple health signals such as pulse rate and waveform, body temperature, muscle movements, and chemicals released from body over time. The monitored signals can be used at one place for diagnosis and treatment.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 1A is a schematic drawing of core-shell conductive nanofibers with electrical junctions between their conductive shells, and a plurality of core-shell nanofibers in an encapsulating polymer matrix.

FIG. 1B is a schematic drawing of the core-shell conductive nanofibers depicted in FIG. 1A under no stress.

FIG. 1C is a schematic drawing of the core-shell conductive nanofibers depicted in FIG. 1A under strain in the direction shown that modifies the resistance of the nanofiber web due to reversible connections and disconnections of electrical junctions FIG. 1D is SEM photomicrographs of core-shell (Au-PAN) conductive nanofiber mesh.

FIG. 1E is a schematic drawing showing a mechanism of disjoint of inter-NF junctions caused by strain which result in changes happened in the current path and increase in resistivity of the sensor.

FIG. 2 is photomicrographs of (a) an encapsulated nanofiber textile strain sensor with electrical contacts and (b) a series of parallel nanofiber textile sensors with separate electrical contacts.

FIG. 7A is a schematic diagram showing an electronic touch sensing skin connected to a readout system.

FIG. 7B is a photograph of a stretchable electronic skin with embedded (two-layered) cross-shape biaxial sensors, according to an embodiment of the invention.

FIG. 7C is a graph of response of the central sensor (22, downward) in a 3×3 sensor to tapping, when 5 taps are made from the upper-left corner to the lower-right corner.

FIG. 7D is a graph of response of the same sensor, when 5 taps are made from the lower-left corner to the upper-right corner, showing smaller amplitude for the off-center taps, indicating the directionality of the response of the sensor.

FIG. 10A is a graph showing Lumbar lateral flexion detected and monitored by sensor 2 and 3 placed on lateral side of midline.

FIG. 10B is a plot showing the switching behaviour of the sensor depends on the lateral flexion direction.

FIG. 11A is a graph Monitoring of lumbar rotation using sensor 2 and 3 on the lateral sides FIG. 11B is a plot showing the relative resistivity showing the switching behaviour the higher signal from rotation from left could be because of miss-alignment of the sensors.

DETAILED DESCRIPTION

The invention described here presents a highly sensitive, low cost, low noise, scalable to large area, and customizable shape fibrous sensor that can be adhered, laminated or attached on different objects or substrates and provide great advantage over the state-of-the-art as mentioned above.

Figure 3:
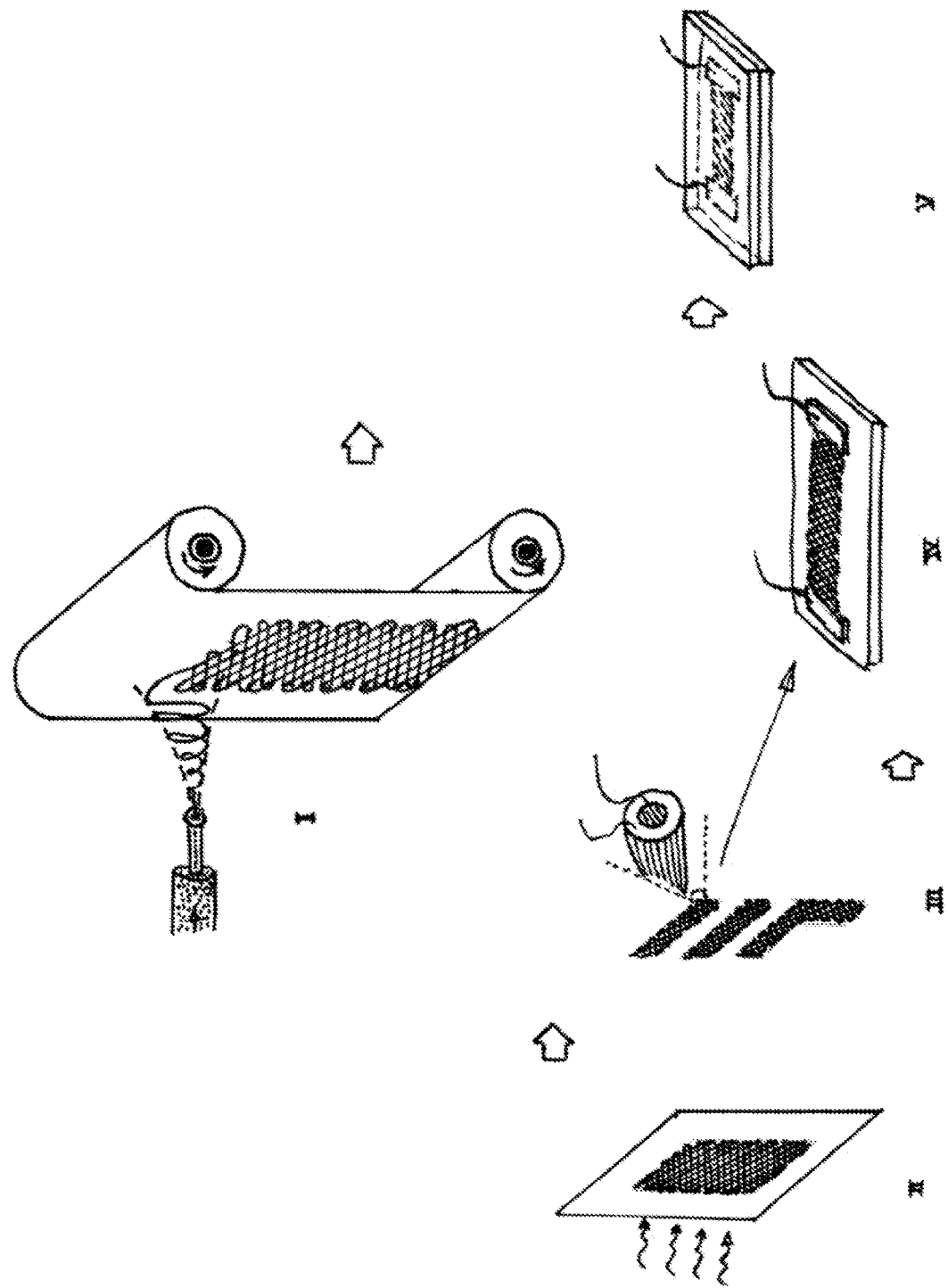
FIG. 3 is schematic diagrams showing various steps of a fabrication process: (I) Deposition of electrospun core of nanofibers in form of a web deposited on a carrier substrate (for example, by roll-to-roll deposition), (II) coating of the nanofiber web with conductive shell to form core-shell nanofiber structures, (Ill) cutting core-shell nanofiber webs into desired shapes, (IV) placing the nanofibers on a the surface of an encapsulation film and formation of electrical contacts that define the direction of current flow, and (V) deposition and curing of the second encapsulation film.

The nanofibers used in this invention are fabricated using a scalable fiber spinning process, including but not limited to, electrospinning and force spinning processes, which result in controlled diameter (10-1000 nm), continuous nanofibers (centimeters long) at low cost. The diameter, density and alignment of the fibers can be accurately controlled by setting parameters of the fiber spinning process as known to the expert in the field. As shown in FIGS. 1, 2 and 3, the fiber meshes are then used as a template and coated with a metallic coating, including but not limited to, gold, copper, silver, aluminum, and nickel, to form a core-shell nanofiber structure, with a highly conductive shell. The conductive shell for the fiber structure can be coated through several methods including metal sputtering, evaporation, electrochemical deposition and also during the fiber spinning process by using methods including but not limited to fiber coaxial co-electrospinning process.

The invention described here presents application of a highly sensitive, low cost, low noise, scalable to large area, and customizable shape fibrous sensor that can be adhered, laminated or attached to the body skin for musculoskeletal, vital signs, body movements and other health related monitoring.

The core provides the nanofiber definition of the mesh and mechanical durability and stretchability, while the shell provides exceptional conduction on the surface of the nanofiber mesh. In addition, the conductive shell of fibers form a large number of interfiber electrical junctions as shown in FIG. 1. The fiber mesh is then cut into the desired shape and placed on the substrate of interest (for example elastomer or hard epoxy resin) and electric contacts are printed or attached to the mesh (for example by using a silver paste or silver particle ink) and connected to wires. Finally, after formation of wiring and contacts, a final elastomer film is coated to encapsulate the sensor. The resulting devices is a strain sensor with a highly sensitive response, low noise and low cost of manufacturing.

This invention is related to a web of core-shell ultrafine nanofibers as schematically drawn in FIG. 1 (a)-(d). The nanofibers have a mechanically robust polymer or polymer composite core, made from, including but not limited to, polyacrylonitrile (PAN), and a highly conductive or a metallic shell, made from, including but not limited to, gold. The diameter of the core can be in the order of 1-1000 nm, for example, 200 nm, and the shell thickness can be in the order of 1-500 nm, for example, 50 nm, as shown in FIG. 1 (d) under a scanning electron microscope (SEM). As shown in FIG. 1, a random or semi-aligned web of core-shell nanofibers is placed between a top and bottom encapsulation films. As a result, the conductive shell of each nanofiber will make electrical junctions to conductive shell of other nanofibers. Upon application of planar tensile strain, as shown in FIG. 1 (e), the electrical junctions between shells of different nanofibers can be reversibly connected or disconnected. This results in a change in the conductance of the web that can provide information on the applied strain, as a strain sensor.

The resistance of the nanofiber web can be monitored by fabrication of two electrical contacts on the ends of a piece of the web. The contacts can be connected to external wirings embedded in the encapsulating films or coming out as shown in FIG. 2. By application of a voltage or current, and measuring the current or voltage, respectively, one can find the resistance of the nanofiber web connecting the two contacts. Changes in the measured resistance can be related to the changes in the mechanical strain or stress. An important aspect of this invention is the low resistance nature (1-10,000 Ohms) of this sensor that can improve signal-to-noise ratio (SNR), repeatability of measurement, and speed of measurement in comparison to other prior arts with much higher resistances (>10,000 Ohms). As shown in FIG. 2, multiple sensors can be integrated between two encapsulation films for location dependent strain monitoring like a sensing skin. In addition, in other embodiments of this invention, the external wiring can be replaced by a wireless measurement of the conductance of the web through addition of an antenna and measurement of resonance frequency of the antenna coupled to the web by an expert in the art.

FIG. 3 demonstrates the manufacturing method of the nanofiber sensor. As shown, the proposed devices is comprised of polymer based ultrafine fibers deposited using a scalable electrospinning, force spinning or other processes that result in controlled diameter at low cost. The diameter, density and alignment of the fibers can be accurately controlled by setting parameters of the electrospinning or the low cost processes used for the deposition of fibrous meshes. After electrospinning of ultrafine continuous nanofibers from polymer or composite solution (step I), the thin web of nanofibers are then used as a template and coated with a conductive coating (e.g., metals like gold, copper, silver, aluminum or conductive polymers or composites) to form a core-shell structure (step II). The core provides the nanofiber definition of the mesh and mechanical durability and stretchability, while the shell provides exceptional conduction on the surface of the nanofiber mesh. The formation of the conductive shell for the fiber structure can be achieved through several methods including metal sputtering, evaporation, electrochemical deposition and coaxial co-electrospinning. The mesh is then cut (step III) into the desired shape and placed on (step IV) the substrate of interest (for example plastic or elastic material (e.g., polydimethylsiloxane (PDMS)) and electric contacts are printed or attached to the mesh (for example by using a silver paste) and connected to wires. The electrical contacts determine the direction of electric current and as a result their location are important for the orientation-dependent strain monitoring. Finally, after formation of wiring and contacts, a final encapsulating film is coated and cured to cover the sensor (step V). The sensor is then cured to hold the composite textile in place and provide a good adhesion to the desired substrate (e.g., glass, metal plates, composite structures, metal blades, etc.).

For example, in step I, a 10 wt. % solution of polyacrylonitrile (MW 100,000 g/mol, Scientific Polymer Products) in dimethylformamide (DMF) (99.9%, Fisher Scientific) is stirred at 60° C. for 24 h, and loaded into a syringe with a blunted G18 needle in an electrospinning unit (Kato Tech Co.) to deposit the nanofibrous mesh on a grounded collector (aluminum foil) at the flow rate and the voltage of 0.6 ml/h and 17 kV, respectively. In step II, a thin conformal gold shell is sputtered (Edward Sputter Coater) on the NF mesh template. Active ribbons of NF mesh with desired dimension (e.g., 3 mm wide and 10-50 mm long) are cut (step III) and transferred (step IV) to the surface of a flat polydimethylsiloxane (PDMS) substrate (first encapsulating film), with a thickness of ~1 mm. Electrical contact pads may be prepared (V) by application of silver pint (Ted Pella) to both ends of the NF mesh. A PDMS layer (2nd encapsulating film) is poured (VI) on the top of the NF mesh and the sample is placed in a desiccator and evacuated by a rotary pump to remove the trapped gas bubbles and obtain a uniform composite, followed by a curing step (VII) at 90° C. for 45 minutes.

A person skilled in the art will also understand that it is possible to spin both layers using co-electrospinning process to create a core-shell fiber. It further is possible to deposit this on the first encapsulating layer.

Figure 4:
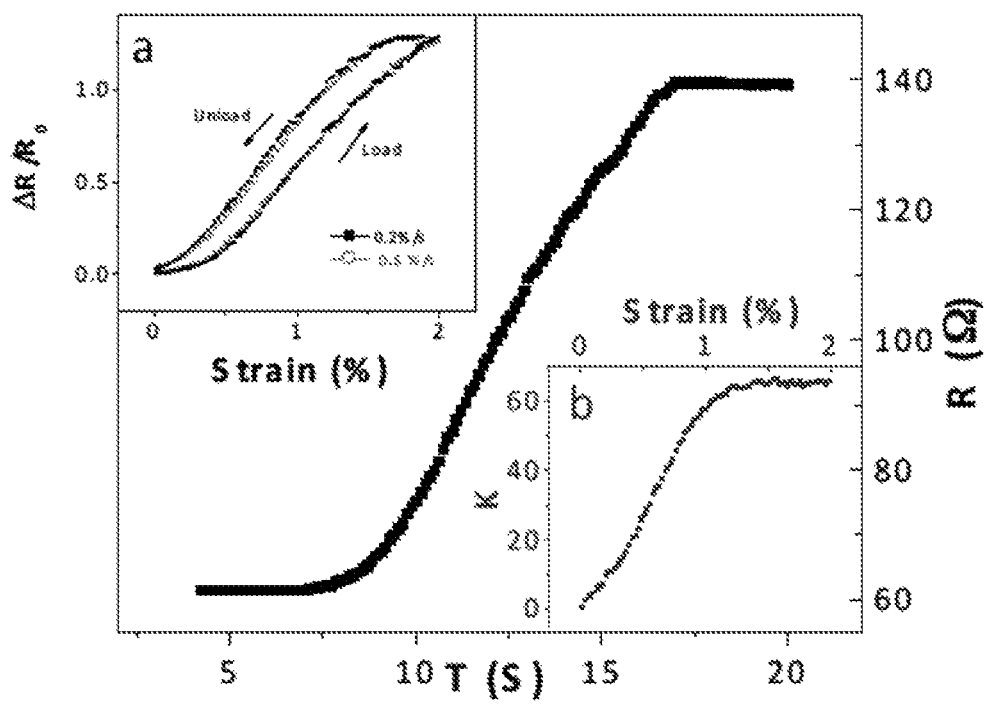
FIG. 4 is graphs showing measured change in the resistance of a typical strain sensor when monotonically stretched from a relaxed position to 2% tensile strain position as a function of time T. Inset (a) depicts the normalized change in resistance as a function of strain during load and unloading. Inset (b) is the gauge factor K as a function of strain.
Figure 5:
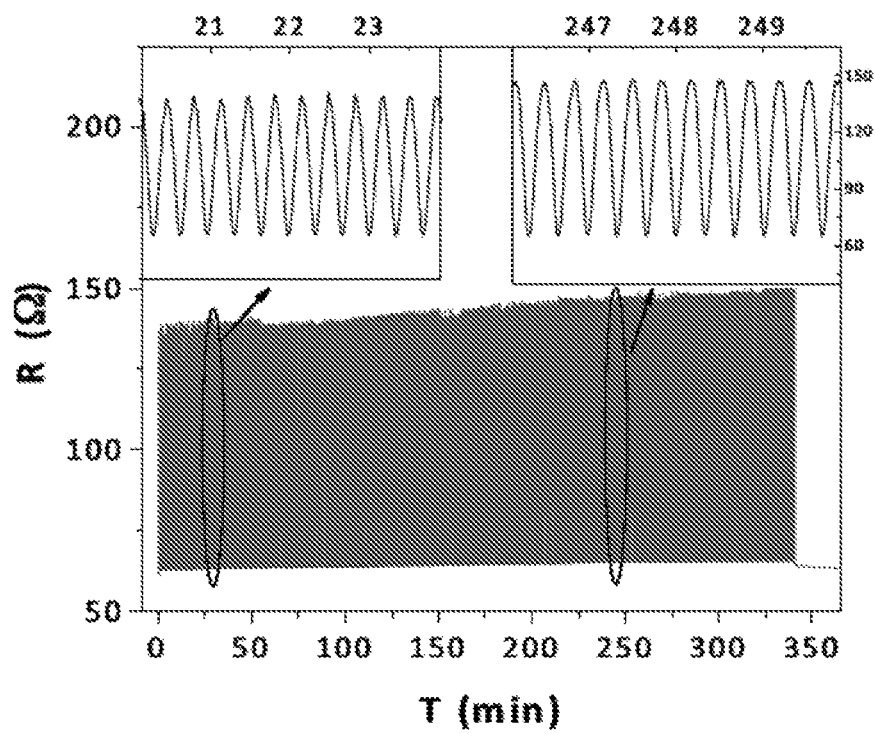
FIG. 5 is graphs showing measured changes in resistance of a typical strain sensor that undergoes repeated (1000 cycles) stretching from a relaxed position to 2% tensile strain position, followed by gradual release of the strain as a function of time T. The insets shows these changes with more accuracy as a function of time.

As shown in FIG. 4, the sensor can monitor the strain over a large dynamic range, from low strains <0.01% to high strain levels >100%, depending on the choice of encapsulating film. The sensor forms a highly-sensitive, low threshold, stretchable mechanical sensor with a gauge factor that can exceed 50 and can be stretched in excess of 100% depending on the properties of the polymer matrix. Such high gauge factors (GF) can only be achieved in conventional systems using piezoelectric materials. But, in this invention a low cost core-shell nanofiber web provides this high GF due to the formation of reversible connections and disconnections in electrical junctions between different nanofibers. The polymer holds the point of contact for each electrical junction together similar to "tensegrity" systems, thus providing a highly reliable and accurate performance over large strains. Also another reason behind the high GF is the reversible cracking of metallic shells of core-shell nanofibers with strain. The low resistance of the sensor in combination with the high GF enables low noise and fast measurement of the changes in strain, not possible by prior art. FIG. 5 illustrates the electrical response of a typical nanofiber strain sensor that undergoes 1000 repeated cycles of relaxation and tensile stretching to 2%.

Figure 6:
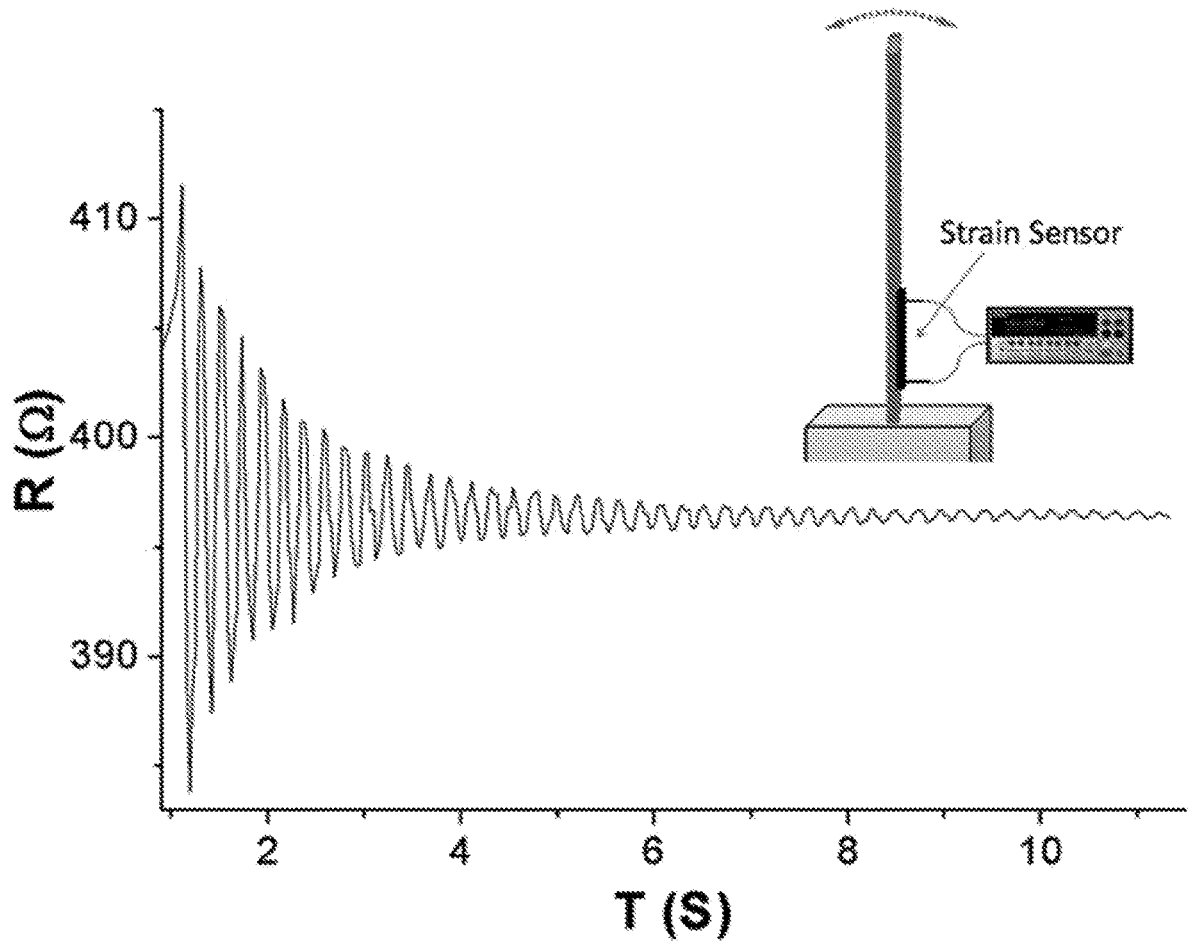
FIG. 6 is a graph showing measured changes in resistance due to vibrations of a rigid metallic blade, signifying the response of the sensor to both tensile and compression strains.

In an embodiment of the present invention, the sensor can be attached to a rigid material (like a metallic blade) for monitoring of the strain. For example, as shown in FIG. 6, by placing the sensor on a metallic blade that is clamped on one side, the resistance of the sensor changes reliably by vibration of the blade, resulting from the tensile and compressive loading of the strain sensor on one of the surfaces of the blade. This shows the performance of the sensor for both tensile and compressive strains in addition to fast response required for vibrational monitoring.

In another embodiment of the present invention, nanofiber sensors are integrated in an encapsulating film in form of a cross, for monitoring strain in a biaxial design, as shown in FIG. 7. This is done by making a first encapsulation substrate, followed by integration of a first layer of nanofiber sensors in one direction. Then, the sensors are coated with a second layer of encapsulating film. This is followed by integration of the second layer of nanofiber sensors in the direction perpendicular to the first direction. Finally, a third encapsulation layer is coated for the completion of the array. An array of biaxial sensors with nine crosses is shown in this figure. The electrical response of the sensor located in the center (22) of the array pointing downward (from the top-left to the bottom-right direction) in two cases. First, as shown FIG. 7(c), five equally spaced taps are made on the array from the left-top corner to the right-bottom corner. The maximum electrical response is for the third tap, which is on top of the sensor being monitored and cause maximum strain on this sensor. In the second experiment, as shown in FIG. 7 (d), five taps are made on the array this time from the left-bottom corner to the right-top corner while monitoring the same downward central sensor. As seen, this time the magnitude of the third tap remains the same, while the other off-center taps generate less response on the sensor due to the directionality of the strain monitoring sensors. As seen, the sensor can accurately show biaxial cognition of the location of strain, which can be used for triangulating the location of tapping and the amount of strain.

Figure 8:
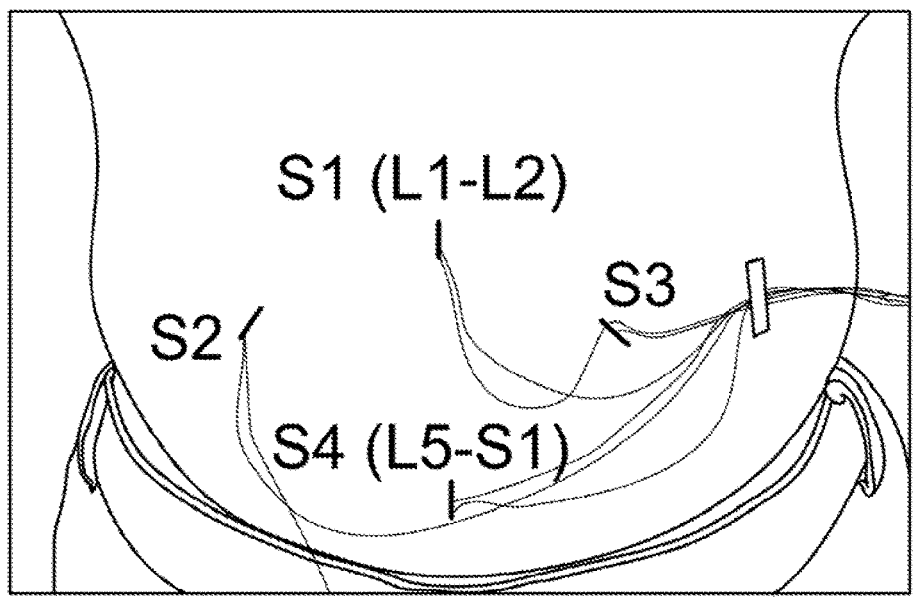
FIG. 8 is a photograph showing the design and sensor placement of strain sensors for segmental monitoring of lumbar spine movements. Sensor 1 is placed in the midline around the L1 vertebrae, which reflect movements of upper lumbar region (UL), Sensor 2 and 3 is placed on the lateral sides of the midline for monitoring of lateral flexion and rotation of the lumbar spine. Sensor 4 is placed on L5-S2 region or lower lumbar (LL).
Figure 9A:
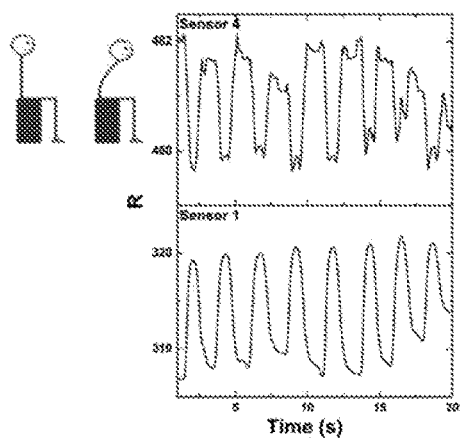
FIG. 9A is a graph showing segmental monitoring of lumbar spine during flexion (slump sitting)
Figure 9B:
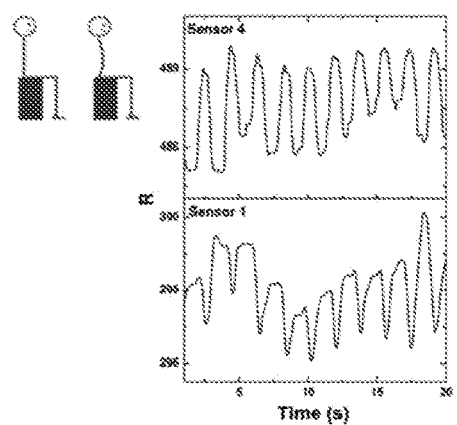
FIG. 9B is a graph showing segmental monitoring of lumbar spine during extension.
Figure 9C:
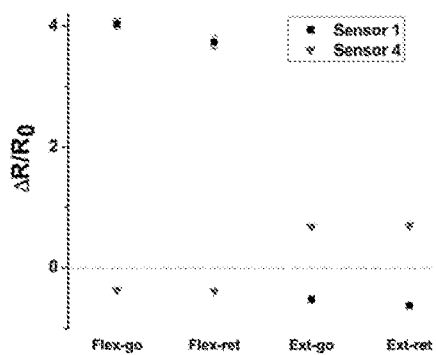
FIG. 9C is a plot showing the relative resistivity during flexion and extension showing the differences between upper lumbar and lower lumbar region.
Figure 9D:
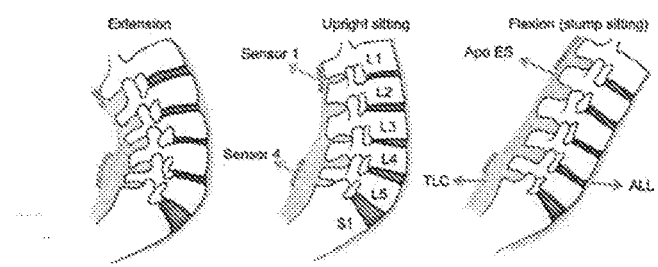
FIG. 9D is a schematic diagram of a proposed mechanism of why sensor 1 and 4 have opposite behaviour caused by involvement of thoracolumbar fascia in lumbar movements.

In this invention we demonstrate the above-described sensors for different monitoring applications. First of all we applied these sensors for segmental monitoring of the lumbar region movements. Low back pain (LBP) is one of the most common reason for compensations claims and it is also one of the most common cause of disabilities, therefore ability to monitor this region could have huge effect on LBP management. FIG. 8 demonstrates the design and sensor placement of the sensors used for lumbar spine monitoring. Sensor 1 is placed on the proximity of L1-L2 vertebrae in the midline of the back and is reflecting the upper lumbar (UL) behaviour especially during sagittal flexion and extension of lumbar region. Sensor 2 and 3 is placed on the lateral side of the midline with a 45 degree angle in the right and left of the midline respectively. These 2 sensors applied for monitoring of lumbar lateral flexion and rotation movements. Finally we applied sensor 4 on top of the L5-S1 region in the midline reflecting the lower lumbar (LL) region.

As shown in FIGS. 9 (a) and (b), the responses of sensor 1 and sensor 4 during the lumbar flexion (slump sitting) and lumbar extension. Sensor 1 shows positive resistivity change during flexion and negative during extension. On the other hand sensor 4 behave in opposite way as it is produced negative changes during flexion and positive resistivity during extension. FIG. 9 (c) illustrated the relative resistivity of sensor 1 and 4 during flexion and extension, which confirmed the opposite behaviour of the upper and lower lumbar segment. It also shows that UL region have a wider range during flexion compare to LL but the movement range of UL and LL region is very similar during extension and is limited compare to flexion of UL region. The reason behind the different behaviour of UL and LL region is the role of the thoracolumbar fascia (TFL) which is become the thoracolumbar composite (TLC) in the LL lumbar region. As illustrated in FIG. 9 (d), because of the lumbar lordosis during the normal sitting caused by paraspinal muscles including the erector spine muscles, the TLC is bulged back slightly. During flexion while sensor 1 is strained because of increasing curvature of the UL region. TLC is tightening during flexion and worked like a string to help body back into extension, therefore the bulging of the TLC decreased and caused the sensor 4 to contract during flexion. The opposite happened in TLC and UL region during extension resulting in contraction of sensor 1 and strain in sensor 4. This shows the possibility of segmental monitoring of the UL and LL regions.

FIG. 10 (a) shown the responses of the sensor 2 and 3 placed on the lateral sides of the lumbar region during the lateral flexion, which mainly caused by lattismus dorsi. The sensors are alternatively strained and contracted depends on the side of lateral flexion to the right or left. The relative resistivity of the sensors is illustrated in FIG. 10 (b), showing the switching behaviour of the sensor 2 and 3 during alternate lateral flexion to the right and the left. FIG. 11 (a) pictured the response of sensor 2 and 3 during lumbar rotation. FIG. 11 (b) shown the relative resistivity calculated for sensor 2 and 3 during rotation, it is still showing the switching behaviour of the sensors but both of them respond stronger for the rotation toward left which could be caused by misalignment of the sensors during the experiment and showing the sensitivity of the sensors for segmental musculoskeletal monitoring.

Figure 12:
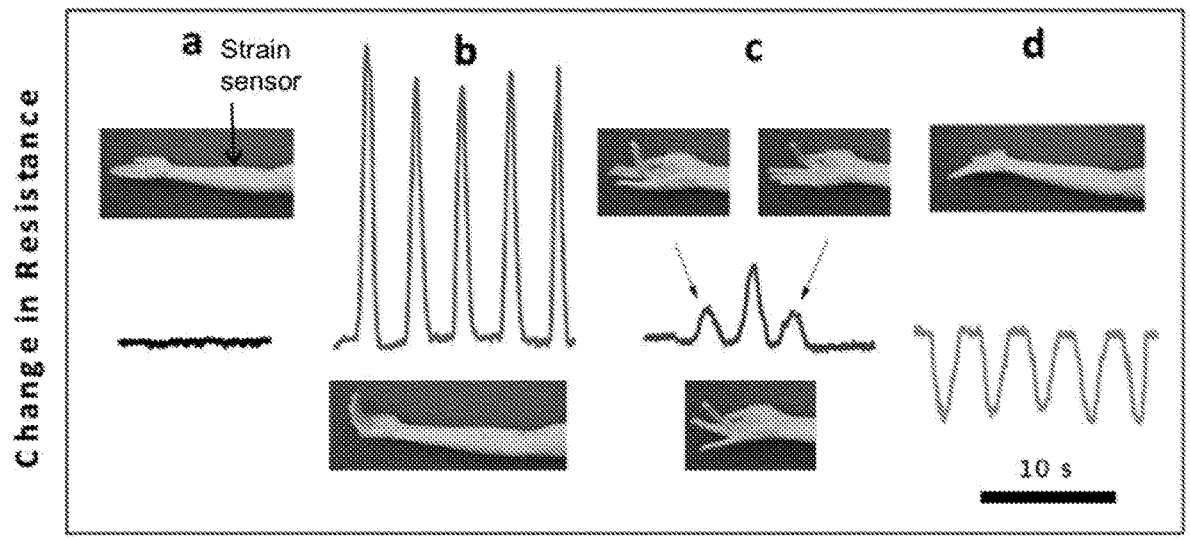
FIG. 12 is graphs showing the response of a nanofiber sensor adhered to epidermis to contractions of the flexor bundle of the forearm muscles for three different finger movements: (I) the neutral hand position (the baseline), (II) repeated flexion and release of all four fingers, (Ill) subsequent flexion of the 2nd, 3rd and 4th digits, and (IV) the repeated extension of all four fingers.

FIG. 12 illustrates our measurements for monitoring of the movements and contractions of flexor bundle of forearm muscles in response to flexions and extensions of the fingers. For this purpose a strain sensor is adhered by a double-sided tape on the ventral side of the forearm in the mid-proximal of the flexor bundle, 10 cm distal from the elbow, parallel to the arm direction. The main muscles involved in the flexion of the fingers are flexor digitrum superficiallis (FDS) and flexor digitrum profondus (FDP), together referred to as the flexor bundle. As shown in FIG. 6, in contrast to relaxed hand (I), five consecutive flexions and releases (II) of all four fingers other than thumb result in abrupt increases in the resistance (indicative of tensile strain due to contraction and increase in the volume of the muscle bundle underneath the sensor) with an accurate correlation to the movements of the fingers. In the next sequence (III), the sensor responds to the sequential one-by-one flexion of 2nd, 3rd and 4th fingers. As seen, the flexion of the 3rd finger produces the highest change in the resistance, as compared to those for the others. The medial side of the flexor bundle moves the 5th and 4th digits and the lateral part of the bundle flexes the 3rd and 2nd digits. Since the flexion of each finger is accompanied by semi-flexion of neighboring fingers through 'enslavement', the sensor shows the highest change for the 3rd finger as it is placed in the middle of the flexor bundle. Interestingly, this sensor reacts to the extension of all four fingers, as well, with a decrease in resistance, which is indicative of a compressive strain due to the contraction of the extension bundle (on the back of the forearm), including extensor digitorum (ED) and extensor digiti minimi (EDM) muscles. During this process, the flexor bundle extends so as to provide the required range of motion for the fingers, resulting in the observed negative response. The ability of the sensors to accurately detect not only the contraction but also the extension is critical for clinical applications as muscle injuries occur more often during extensions.

Figure 13A:
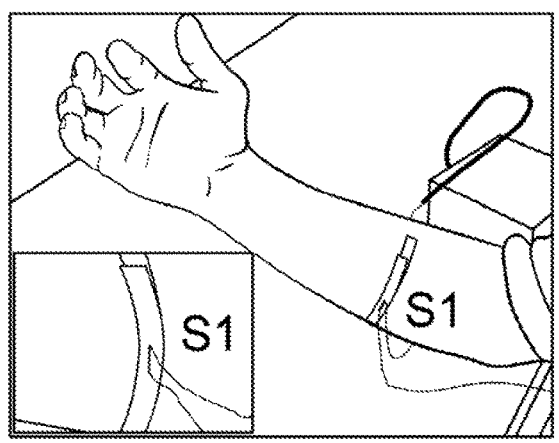
FIG. 13A is a picture showing application of a strain sensor placed on the flexor bundle of forearm for monitoring of the simulated Parkinson's hand tremor.
Figure 13B:
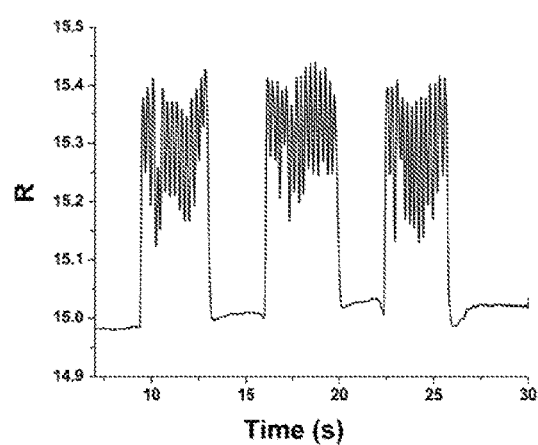
FIG. 13B is a graph showing monitoring of the simulated Parkinson's hand tremor.

Using the same sensor attached to the flexor bundle of the forearm we manage to noninvasively monitor simulated Parkinson's hand tremor. FIG. 13 shown the intermittent vibrational peaks detected from the hand tremor. This technique has huge potential for long-term remote monitoring of the neurological signs such as Parkinson and can provide feedback for better controlling and medication of chronic illnesses and rehabilitation.

Figure 14A:
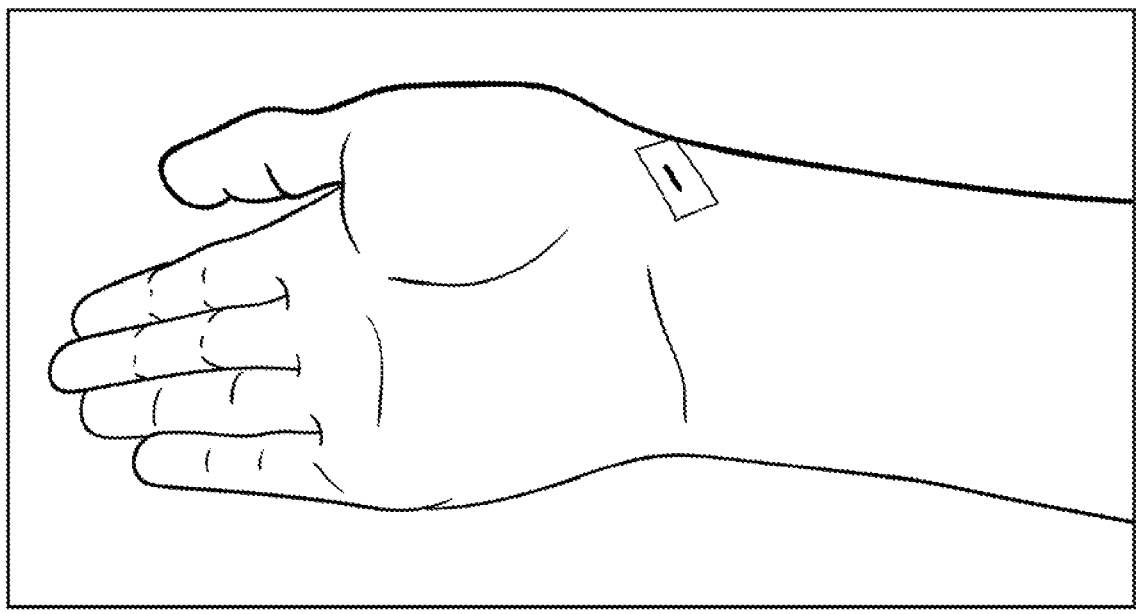
FIG. 14A is a picture showing application of a strain sensor adhered at the wrist for monitoring of the radial pulse
Figure 14B:
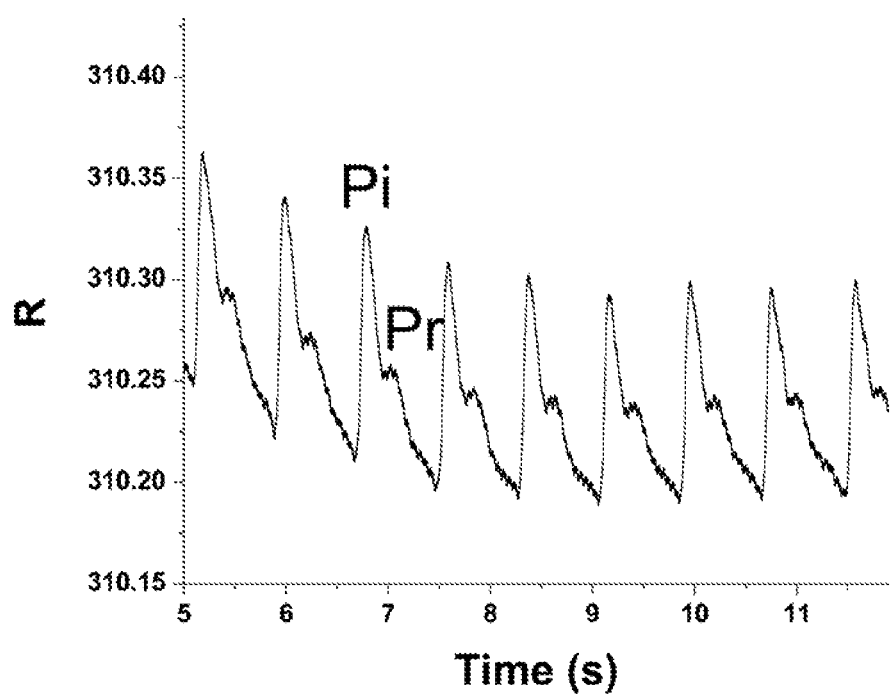
FIG. 14B is a graph showing the monitoring of the radial pulse using the setup depicted in FIG. 14A. The graph shows a rate of 65 beats per minute and distinguishable systolic incident wave (Pi) and diastolic reflected wave (Pr).

Real-time monitoring of radial pulse using a sensor directly placed on radial artery is illustrated in FIG. 14. Resting heart beat is detected and the pulse rate is calculated to be around 80 beats per minute. Interestingly, waveform obtained for each pulse shows an early systolic peak, FIG. 14 (b) (Pi), produced by forward ejection of blood along a direct pass from left ventricle to the hand, followed by a later peak, FIG. 14 (b) (Pr), happened in early diastole which is mainly formed by backward wave reflected from any point of impedance discontinuity such as arterial branching and arterial-arteriolar junctions. This is consistent with results of well-established methods of pulse wave analysis (PWA) and pulse wave velocity (PWV) measurements using photoplethysmography and applanation tonometry. The ability to non-invasively and accurately detect pulse rates at the wrist demonstrates the potential for sensitive epidermal and wearable electronic monitoring of vital signs in emergency medicine and intensive care units.

The data gathered about vital and physiological signs can be gathered and communicated wirelessly or with wires for further analysis and diagnostics.

The sensors can be attached to body or worn using compression fitted fabric.

While specific embodiments of the invention have been described and illustrated, such embodiments should be considered illustrative of the invention only and not as limiting the invention as construed in accordance with the accompanying claims.

The invention claimed is:

1. A resistive sensor system comprising:
   at least one resistive sensor device, each resistive sensor device of the at least one resistive sensor device comprising:
   a fiber mesh comprising a plurality of elongate fibers, wherein each fiber of the plurality of fibers comprises an electrical conductor comprising an electrically conductive exterior surface reversibly positionable into and out of electrically conductive contact with the electrically conductive exterior surfaces of adjacent fibers of the plurality of fibers;
   at least one resiliently deformable encapsulating film that encapsulates the fiber mesh, whereby resilient deformation of the at least one encapsulating film moves fibers of the plurality of fibers and reversibly controls electrically conductive contact between the exterior surfaces of adjacent fibers of the plurality of fibers and changes electrical resistance of the fiber mesh;
   a first electrical contact electrically coupled to the electrical conductor of at least one of the plurality of fibers; and
   a second electrical contact electrically coupled to the electrical conductor of at least one of the plurality of fibers and spaced apart from first electrical contact, whereby the first and second electrical contacts are positioned to apply an electrical voltage or current across at least a portion of the fiber mesh; and
   a monitoring and readout system programmed to, at least, identify:

changes in resistance between the first and second electrical contacts of each resistive sensor device of the at least one resistive sensor device; and deformation of the at least one resiliently deformable encapsulating film of each resistive sensor device of the at least one resistive sensor device by analysis of the changes in the resistance between the first and second electrical contacts of each resistive sensor device of the at least one resistive sensor device.

2. The system of claim 1 wherein the at least one resistive sensor device comprises a plurality of resistive sensor devices.

3. The system of claim 1 wherein the monitoring and readout system is further programmed to identify, by analysis of the deformation, a blood pressure of a human or an animal wearing the at least one resistive sensor device.

4. The system of claim 1 wherein the monitoring and readout system is further programmed to identify, by analysis of the deformation, changes in muscle volume of at least one muscle of a human or an animal wearing the at least one resistive sensor device.

5. The system of claim 1 wherein the monitoring and readout system is further programmed to identify, by analysis of the deformation, a heart rate of a human or an animal wearing the at least one resistive sensor device.

6. The system of claim 1 wherein the monitoring and readout system is further programmed to identify, by analysis of the deformation, a respiration rate of a human or an animal wearing the at least one resistive sensor device.

7. The system of claim 1 wherein the monitoring and readout system is further programmed to identify, by analysis of the deformation, movement of fingers of a human wearing the at least one resistive sensor device in response to identifying movements of muscles of a forearm of the human.

8. The system of claim 1 wherein the at least one resiliently deformable encapsulating film of the at least one resistive sensor device is attached to or embedded in a flexible or stretchable object positionable to contact a tissue of a human or an animal.

9. The system of claim 8 wherein the object is clothing.

10. The system of claim 8 wherein the object is a wrist band.

11. The system of claim 8 wherein the object is a cuff positionable on a limb of the human or of the animal.

12. The system of claim 8 wherein the object is an adhesive body configured to be adhered to another object.

13. The system of claim 8 wherein the monitoring and readout system is programmed to identify a location, magnitude, or direction of the deformation.

14. A method of monitoring movements of a human or an animal, the method comprising:

when the at least one resiliently deformable encapsulating film of each resistive sensor device of the at least one resistive sensor device of claim 1 is worn by the human or the animal, causing the monitoring and readout system to identify the deformation of the at least one resiliently deformable encapsulating film of each resistive sensor device of the at least one resistive sensor device by the analysis of the changes in the resistance between the first and second electrical contacts of each resistive sensor device of the at least one resistive sensor device.

15. The method of claim 14, wherein the at least one resistive sensor device comprises a plurality of resistive sensor devices.

16. The method of claim 14 further comprising causing the monitoring and readout system to identify, by analysis of the deformation, a blood pressure of the human or the animal.

17. The method of claim 14 further comprising causing the monitoring and readout system to identify, by analysis of the deformation, changes in muscle volume of at least one muscle of the human or the animal.

18. The method of claim 14 further comprising causing the monitoring and readout system to identify, by analysis of the deformation, a heart rate of the human or the animal.

19. The method of claim 14 further comprising causing the monitoring and readout system to identify, by analysis of the deformation, a respiration rate of the human or the animal.

20. The method of claim 14 wherein the animal is a human.

21. The method of claim 20 further comprising causing the monitoring and readout system to identify, by analysis of the deformation, movement of fingers of the human in response to identifying movements of muscles of a forearm of the human by the analysis of the deformation.

* * * * *